US010145826B2

(12) United States Patent
Haarer et al.

(10) Patent No.: US 10,145,826 B2
(45) Date of Patent: Dec. 4, 2018

(54) TIME TEMPERATURE INDICATOR

(71) Applicant: FRESHPOINT QUALITY ASSURANCE LTD., Nesher, Haifa (IL)

(72) Inventors: Dietrich Haarer, Bayreuth (DE); Tal Gueta-Neyroud, Haifa (IL); Husein Salman, Rajar (IL)

(73) Assignee: FRESHPOINT QUALITY ASSURANCE LTD., Nesher (IL)

( * ) Notice: Subject to any disclaimer, the term of this patent is extended or adjusted under 35 U.S.C. 154(b) by 444 days.

(21) Appl. No.: 14/691,399

(22) Filed: Apr. 20, 2015

(65) Prior Publication Data

US 2015/0226715 A1 Aug. 13, 2015

Related U.S. Application Data

(63) Continuation of application No. 12/522,562, filed as application No. PCT/EP2007/064595 on Dec. 28, 2007, now Pat. No. 9,011,794.

(30) Foreign Application Priority Data

Jan. 11, 2007 (EP) .................................. 07100418.8
Aug. 9, 2007 (EP) .................................. 07114081.8

(51) Int. Cl.
G01N 31/00 (2006.01)
G01N 31/22 (2006.01)
(Continued)

(52) U.S. Cl.
CPC ............. G01N 31/229 (2013.01); G01K 3/04 (2013.01); G01K 11/12 (2013.01); G01N 21/78 (2013.01);
(Continued)

(58) Field of Classification Search
CPC .................................................... G01N 31/229
(Continued)

(56) References Cited

U.S. PATENT DOCUMENTS 3,591,810 A 7/1971 Jackson
4,382,700 A 5/1983 Youngren
(Continued)

FOREIGN PATENT DOCUMENTS

EP 0276335 3/1988
EP 898202 2/1999
(Continued)

OTHER PUBLICATIONS

U.S. Appl. No. 61/130,928 to Gordhanbhai N. Patel, filed Jun. 4, 2008; publicly available Dec. 10, 2009.
(Continued)

Primary Examiner — Christine T Mui
Assistant Examiner — Emily R. Berkeley
(74) Attorney, Agent, or Firm — Browdy and Neimark, PLLC.

(57) ABSTRACT

The present invention is generally in the field of measuring and indicating techniques and relates to a time-temperature indicator and methods of manufacturing and use thereof. More specifically, the time-temperature indicator comprises a time temperature indicator comprising at least one metal layer or metal containing layer and in direct contact to the metal layer or to the metal containing layer at least one doped polymer layer, wherein the dopant is an acid, a base or a salt or a photolatent acid or a photolatent base which dopant is added to the polymer, and/or at least one polymer layer wherein a polymer is functionalized with acidic or latent acidic or basic or latent basic groups; or a time temperature indicator comprising at least one polymer layer containing metal particles and a photolatent acid or a pho-
(Continued)

tolatent base, or at least one polymer layer containing metal particles wherein the polymer is functionalized with latent acidic or latent basic groups.

28 Claims, 6 Drawing Sheets

(51) Int. Cl.
    *G01K 3/04* (2006.01)
    *G01K 11/12* (2006.01)
    *G01N 21/78* (2006.01)
    *G01N 21/77* (2006.01)

(52) U.S. Cl.
    CPC ....... *G01N 31/22* (2013.01); *G01N 2021/773* (2013.01); *Y10S 252/962* (2013.01)

(58) Field of Classification Search
    USPC .................................................... 422/400
    See application file for complete search history.

(56) References Cited

U.S. PATENT DOCUMENTS

| | | | |
|---|---|---|---|
| 4,432,656 A | 2/1984 | Allmendinger |
| 4,737,463 A | 4/1988 | Bhattacharjee et al. |
| 4,773,766 A | 9/1988 | Nagasaka et al. |
| 4,816,634 A | 3/1989 | Lentz et al. |
| 4,834,017 A | 5/1989 | Favetto et al. |
| 4,859,360 A | 8/1989 | Suzuki et al. |
| 5,053,339 A | 10/1991 | Patel et al. |
| 5,057,434 A | 10/1991 | Prusik et al. |
| 5,254,473 A | 10/1993 | Patel et al. |
| 5,317,987 A | 6/1994 | Mueller Hubert et al. |
| 5,667,303 A | 9/1997 | Arens et al. |
| 5,722,317 A | 3/1998 | Ghiron et al. |
| 5,747,225 A | 5/1998 | Manica et al. |
| 5,969,606 A | 10/1999 | Reber et al. |
| 6,009,400 A | 12/1999 | Blackman |
| 6,042,264 A | 3/2000 | Prusik |
| 6,242,714 B1 | 6/2001 | Narumiya et al. |
| 6,382,125 B1 | 5/2002 | Tamura |
| 6,435,128 B2 | 8/2002 | Qiu |
| 6,514,462 B1 | 2/2003 | Simons |
| 6,544,925 B1 | 4/2003 | Prusik et al. |
| 6,614,728 B2 | 9/2003 | Spevacek |
| 6,616,332 B1 | 9/2003 | Renken et al. |
| 6,660,345 B2 | 12/2003 | Coates et al. |
| 6,865,516 B1 | 3/2005 | Richardson |
| 6,866,417 B2 | 3/2005 | Gunawardena et al. |
| 6,974,249 B1 | 12/2005 | Fair et al. |
| 7,039,927 B2 | 5/2006 | Constantinou et al. |
| 7,081,364 B1 | 7/2006 | Haarer et al. |
| 7,213,967 B2 | 5/2007 | Simunovic et al. |
| 7,263,501 B2 | 8/2007 | Tirinato et al. |
| 7,476,874 B2 | 1/2009 | Patel |
| 8,343,437 B2 | 1/2013 | Patel |
| 2002/0056751 A1 | 5/2002 | Lee |
| 2002/0085164 A1 | 7/2002 | Stanford-Clark |
| 2003/0139843 A1 | 7/2003 | Hu et al. |
| 2003/0174263 A1 | 9/2003 | Lawandy |
| 2003/0193987 A1 | 10/2003 | Zalameda et al. |
| 2004/0092023 A1 | 5/2004 | Wright |
| 2004/0182932 A1 | 9/2004 | Kawai |
| 2005/0037498 A1 | 2/2005 | Ribi |
| 2005/0139686 A1 | 6/2005 | Helmer et al. |
| 2005/0178841 A1 | 8/2005 | Jones et al. |
| 2005/0261991 A1 | 11/2005 | Kennamer |
| 2006/0032427 A1 | 2/2006 | Ishii et al. |
| 2006/0203882 A1 | 9/2006 | Makela et al. |
| 2007/0172951 A1 | 7/2007 | Levy |
| 2008/0129037 A1 | 6/2008 | Roth et al. |
| 2008/0187021 A1 | 8/2008 | Haarer et al. |

FOREIGN PATENT DOCUMENTS

| | | | | |
|---|---|---|---|---|
| GB | 2423360 A | * | 8/2006 | ............. G01N 21/80 |
| JP | 10046072 A | | 2/1998 | |
| JP | 10334171 A | | 12/1998 | |
| WO | 94/027242 | | 11/1994 | |
| WO | 99/039197 | | 5/1999 | |
| WO | 03/044521 | | 5/2003 | |
| WO | 03/077227 | | 9/2003 | |
| WO | 04/077002 | | 9/2004 | |
| WO | 5/050192 | | 6/2005 | |
| WO | 05/075978 | | 8/2005 | |
| WO | 08/083926 | | 7/2008 | |
| WO | 06/048412 | | 5/2011 | |

OTHER PUBLICATIONS

Eduardo et al., "Photoresponsive polyurethane-acrylate block copolymers. I. Photochromic effects in copolymers containing 6'-nitro spiropyranes and 6'-nitro-bis-spiropyranes" J. Appl. Polymer Science; 71:259-266 (1991).

International Search report for PCT/EP07/064595 dated Apr. 4, 2008.

International Search report for PCT/EP2009/057334 dated Oct. 2, 2009.

International Search report for PCT/IL2004/001 070 dated Mar. 4, 2005.

* cited by examiner

El = electrode

C= O (zero capacitance)

Viscoelastic Fluid

Time Temperature

Viscoelastic Fluid

| Time needed to reach 350 μW at 40°C |||| 
|---|---|---|---|
| Aluminium type | Aluminium | Time (hours) | Time (days) |
| PVD | Kurz skt20 | 12 hours | 0.5 days |
| | Kurz skt35 | 18 hours | 0.75 days |
| | Kurz skt57 | 36 hours | 1.5 days |
| | Kurz skt75 | 43 hours | 1.8 days |
| Ink | Eckart FX1604 | 124 hours | 5.2 days |
| | Eckart GX2550 | 166 hours | 6.9 days |
| | Eckart FX1504 | 175 hours | 7.3 days |
| | Eckart GX2807 | 218 hours | 9.1 days |

TIME TEMPERATURE INDICATOR

This invention is generally in the field of measuring and indicating techniques and relates to a time-temperature indicator and methods of manufacturing, dispensing and reading this indicator.

Time temperature indicators are devices that are characterized by at least one changeable observable property that progresses in a rate that is proportional to the temperature and time, and thus provide an indication of the full or partial time-temperature history of their immediate surroundings to which they are thermally coupled. Time temperature indicators (TTIs) are simple and inexpensive devices, typically designed as labels. When attached to a perishable good, a TTI (appropriately designed and calibrated) monitors its time-temperature history and provides a simple, usually visual, straightforward summary of the exposure history of the product to time-temperature, thereby providing indication of the product freshness condition. Consequently, TTIs are among the most promising shelf-life-report technologies.

The TTI concept was developed to ensure the safety and quality of perishable goods, such as food and drug products, throughout their entire lifespan, from manufacturing or packaging to the time they are consumed by the end user. The safety and quality of many perishable goods such as food, drugs, vaccines and blood, depend mainly on appropriate storage conditions during distribution and storage. Different factors such as gas composition, relative humidity and temperature affect their real lifetime. The fact that changing conditions affect the effective shelf life of these kinds of goods is not reflected by a "best before . . . " type label that relies on appropriate storage conditions. Of all storage factors, temperature abuse is the most frequently observed factor for pre-dated deterioration, based on diverse physical, chemical, enzymatic or microbial processes. Therefore, the TTI technology can provide a simple tool for controlling the food and drug chain. The color and/or other physical properties of the TTI varies as a function of the time at a rate which is temperature dependent, thus providing an active scale of "freshness" of the product to which it is attached, by comparing the color (or darkness) or any other varying visual property of the TTI label with a given comparative scale. Since the TTI indicators may be designed to provide a distinct "Yes" or "No" type of answer regarding the time temperature factor, they may provide an important "clear cut"-answer and save further elaborate data inspection. This is ideal for HACCP (Hazard Analysis Critical Control Point), where the emphasis is on real time decision making and action.

Various TTIs are disclosed for example in the following patent publications:

U.S. Pat. No. 6,435,128 discloses a time-temperature integrating indicator device that provides a visually observable indication of the cumulative thermal exposure of an object. The device includes a substrate having a diffusely light-reflective porous matrix and a backing. The backing includes on its surface a viscoelastic indicator material for contacting the substrate and a barrier material for substantially inhibiting the lateral and longitudinal flow of viscoelastic indicator material between the substrate and the backing.

U.S. Pat. No. 6,042,264 discloses a time-temperature indicator device, designed as a label, for measuring the length of time to which a product has been exposed to a temperature above a pre-determined temperature. The period of time of exposure is integrated with the temperature to which the indicator is exposed. The label is a composite of a plurality of layers adapted to be adhered at its underside to a product container. The label includes a printable surface layer, a longitudinal wicking strip that is adhered underneath the surface layer substantially at the opposite extremities only of the wicking strip and a lower substrate layer forming an envelope with said surface layer. A heat-fusible substance, which melts and flows above a pre-determined temperature, is applied on the surface of the wicking strip contiguous to at least one of the ends of the wicking member. When the heat-fusible substance is exposed to a temperature above the pre-determined temperature, the heat-fusible substance flows along the length of the wicking member. The label has a printable surface layer and is sealed at its peripheral edge to the peripheral edge of the substrate layer. These layers encapsulate the wicking member and the heat-fusible substance. The surface layer is provided with a sight window at an intermediate location over the wicking member through which the progress of flow on the wicking member is observed.

WO 03/077227 discloses a time indicating label comprising a label substrate having first and second surfaces, an acid-based indicator composition, and an activator composition. One of the acid-based indicator composition and the activator composition is on the first surface of the substrate, and both of these compositions when brought in contact remain adhered. The label may have a pressure sensitive adhesive on the second surface of the label. The label provides an effective means for determining the safety of frozen foods. The labels also provide a means of providing security by providing name badges that are time sensitive and may not be reused. The name badges provide a means to monitor the length of a visitor's time and prevent reusing the name badge.

WO 03/044521 discloses a sensor adapted to be remotely readable by RF techniques for identification of the quality of a packaged foodstuff. The sensor either reacts with compounds generated in the atmosphere of the foodstuff package due to the microbiological decay of the foodstuff, for example hydrogen sulfide or other sulfide compounds, or the sensor is responsive to an increased oxygen content in the atmosphere of the package due to a leakage in the package. The sensor is based on a RF circuit. Oxygen or the microbiologically generated gas affects the electrical properties of the circuit material. For example, the resistor, the capacitor or the inductive coil of the circuit or at least a fraction thereof are made of silver, iron, aluminium, a redox-type indicator-dye, a conductive polymer, or copper. Due to the reaction of the aforementioned gases with these materials, the sensor resistance, conductivity, capacitance and/or inductance of the respective sensor elements changes depending on the amount of the disintegrating gas.

WO2006048412 (Freshpoint) describes a time temperature indicator device comprising at least 4 layers, a substrate layer, a salt layer and a metal layer and a polymer layer. The dry salt layer is evaporated atop the substrate layer. The metal is in direct contact with the dry salt layer. The metal layer covers the salt layer entirely to avoid that due to humidity the salt starts to dissolve and affects the metal. Above the metal layer is a layer of a viscoelastic polymer. The viscoelastic polymer has a solid to liquid transition when exposed to temperatures higher than a certain threshold temperature. Being liquid the viscoelastic polymer diffuses through the metal and thus mixes the metal layer and the salt layer. Now the metal layer is etched and changes its thickness and conductivity. The time temperature detection depends on the viscosity of the polymer layer. For different threshold temperatures different polymers are required.

The problem underlying the present invention is to find a TTI which is easily producible and in which the polymer layer can be tuned to different affecting agents, for example etching agents and to different etching rates. In this configuration the TTI can be tailored to different time and temperature regimes by taking different affecting agents and polymers of different viscosity.

The problem is solved by providing (1) a time temperature indicator comprising at least one metal layer or metal containing layer and in direct contact to the metal layer or to the metal containing layer at least one doped polymer layer, wherein the dopant is an acid, a base or a salt or a photolatent acid or a photolatent base which dopant is added to the polymer, and/or at least one polymer layer wherein a polymer is functionalized with acidic or latent acidic or basic or latent basic groups; or (2) a time temperature indicator comprising at least one polymer layer containing metal particles and a photolatent acid or a photolatent base, or at least one polymer layer containing metal particles wherein the polymer is functionalized with latent acidic or latent basic groups.

The doped polymer layer or the functionalized polymer layer in contact with the metal is responsible for the time-temperature dependent changes in the optical, electrical, and/or electronic properties of the TTI and/or one or more of its components.

The doped polymer is, for example, etching, dissolving, fragmenting or decomposing the metal thus causing a change in the optical and/or electrical properties of the metal layer or the metal containing layer.

BRIEF DESCRIPTION OF THE DRAWINGS

FIG. 2 is a schematic illustration of a TTI structure according to one embodiment of the invention, utilizing a capacitive device which is characterized by two conductive layers with a dielectric/insulating layer in between.

FIG. 4B is a schematic illustration of a TTI structure according to the

DEFINITIONS

Figure 1:
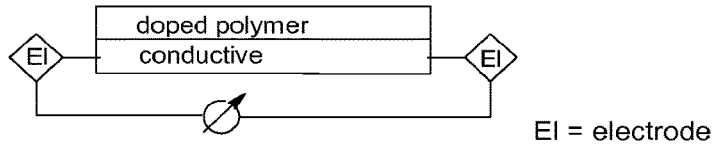
FIG. 1 is a schematic illustration of a resistive TTI comprising one metal layer in contact with a doped polymer layer. The resistance is measured with two electrodes.

Optical properties are, for example, absorption, transmission, reflectivity and the like.

Electrical and/or electronic properties are, for example, conductivity, resistance, capacitance, dielectric constant, inductance, resonance frequency (RF) and the like.

The Polymer

The polymer is the carrier for the dopant and is a homopolymer, a copolymer, an adhesive or a viscoelastic liquid containing at least a polymer of the group consisting of polyethylene imine, polyethyleneglycoles, polysulfonates, polyacrylates, polymethacrylates, polyacrylic acid, polymethacrylic acid, polyvinyl alcohol, polyvinylchloride, polyvinylacetate, polyolefins, polyvinyl ethers, styrene/butadiene latexes, polyisobutylene, polyisoprene, polyurethane, polybutadiene, polychloroprene, butadiene acrylonitrile rubber, poly vinyl aryl phosphonic acid and/or esters, poly vinyl alkyl phosphonic acid and/or esters. The polymer layer may be composed of either one type of a polymer or a mixture of polymers or even a mixture of polymers and oligomers or monomers.

Adhesives are natural adhesives or synthetic adhesives, for example based on elastomers, thermoplastic, and thermosetting adhesives.

Preferred are polyethylene imine, polyethyleneglycoles, polyacrylates, polymethacrylates polysulfonates, poly vinyl aryl phosphonic acid and/or esters, poly vinyl alkyl phosphonic acid and/or esters as well as mixtures thereof.

Especially preferred are polyacrylates and polymethacrylates and polyethyleneimine, mostly polyacrylates and polymethacrylates as well as mixtures thereof.

Suitable additives serving as tackifiers for these polymers are rosin, rosin derivatives, hydrocarbon resins etc. Other additives such as wetting agents, plasticizers, fillers, preservatives and antifoaming agents are in some cases added.

A favoured viscoelastic liquid is prepared from copolymers of the polyacrylate family. The monomer composition of these co-polymers is 50%-90% of a main soft monomer (e.g. ethyl acrylate, n-butyl acrylate, 2-ethylhexyl acrylate, iso-octyl acrylate etc.) which confers a low Tg to the material and thus high tack properties. The material is modified by 10%-40% of a secondary hard co-monomer (e.g. methylmethacrylate, t-butyl methacrylate, vinyl acetate, acrylic acid, etc.), which confers higher Tg to the material and thus higher peel adhesion. Functional monomers inducing crosslinking, improved wetting properties, and adhesion buildup are sometimes added (e.g. acrylic acid, methacrylic acid, itacronic acid, etc.). A preferred polymerization technique is oil in water (o/w) emulsion polymerization initiated by a radical initiator (e.g. ammonium persulfate, sodium persulfate, AIBN, etc.). The polymerization is performed in some cases in the presence of buffering agents which improve the stability of final emulsion and allow a better compatibility of the components (e.g. ammonium hydroxide, sodium hydroxide, disodium phosphate, etc.). The polymerization is performed in the presence of non-ionic and/or ionic surfactants (e.g. sodium lauryl sulphate, fatty alcohol ether sulphates, fatty alcohol polyglycol ether, polyvinyl alcohol, dodecylbenzene sulfonic acid etc.).

The Dopant

In one embodiment the dopant is a salt.

The salt is preferably selected from the group consisting of water soluble salts such as sodium chloride, potassium iodide, lithium fluoride, potassium chloride, sodium iodide, lithium fluoride, sodium carbonate and the like. Mixtures of the salts are also possible.

In one embodiment the dopant is an acid.

The acid is preferably selected from phosphoric acid, nitric acid, hydrochloric acid, sulphuric acid, polyphosphoric acid, pyrophosphoric acid, phosphonic acid, alkyl phosphonic acid (and derivatives), aryl sulfonic acids and alkyl sulfonic acids (and derivatives) and the like. An example of an aryl sulfonic acid may be Dodecyl Benzene Sulfonic Acid (DBSA). Mixtures of the above acids are also possible.

In one embodiment the dopant is a base.

The base is preferably selected from an alkali metal hydroxide, ammonium hydroxide, tetra alkyl ammonium hydroxides, tetra alkyl ammonium fluorides and the like. Mixtures thereof are also possible.

In one embodiment the dopant is a photolatent acid where the acid is released upon irradiation with light.

Some photolatent acids are commercially available and are, for a non limiting example, selected, from the group ESACURE (Lamberti), IRGACURE (Ciba) e.g. IRGACURE® PAG103 (2-methyl-α-[2-[[[(n-propyl)sulfonyl]oxy]imino]-3(2H)-thienylidene]-benzeneacetonitrile 2(5H)-thienylidene]-benzeneacetonitrile), IRGACURE® PAG108 (2-methyl-α-[2-[[[(n-octyl)sulfonyl]oxy]imino]-3(2H)-thienylidene]-benzeneacetonitrile), IRGACURE® PAG121 (2-methyl-α-[2-[[[(4-methylphenyl)sulfonyl]oxy]imino]-3(2H)-thienylidene]-benzeneacetonitrile), IRGACURE® PAG203, Ethanone, 1,1'-[1,3-propanediylbis(oxy-4,1-phenylene)]bis-[2,2,2-trifluoro-bis[O-(propylsulfonyl)oxime], UVI (DOW), CYRACURE (DOW), 2-(-Methoxystyryl)-4,6-bis(trichloro-methyl)-1,3,5-triazine (Aldrich), sulfonates photoacid generators (Midori Kagaku).

In one embodiment the dopant is a photolatent base where the base is released upon irradiation with light.

Some photolatent bases are commercially available and are, for a non limiting example, IRGACURE (Ciba) such as for example, IRGACURE® 369 (2-Benzyl-2-(dimethyl-amino)-1-[4-(4-morpholinyl)phenyl]-1-butanone as described in EP 898202 or IRGACURE® 907 (2-Methyl-1-[4-(methylthio)phenyl]-2-(4-morpholinyl)-1-propanone).

In yet other embodiments, the polymer is a functionalized polymer, functionalized with acidic or latent acidic or basic or latent basic groups. These groups are chemically attached to the polymer, forming the "reactive polymer".

A non limiting example for the photo production of phosphoric acid is presented here as a non-restrictive example of the formation of an acid upon irradiation:

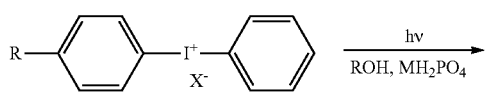

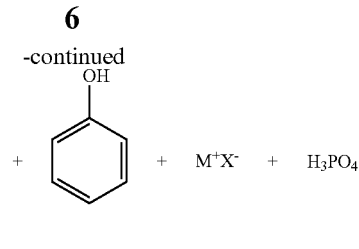

In some embodiments, it is preferable to use photosensitizers such as ITX for improved spectral sensitivity and quantum yields for the photoprocess.

The dopant is added to the polymer layer, to the adhesive, or to the viscoelastic liquid thus obtaining a "reactive polymer" which affects the metal due to its salt content or due to its acid or base content. The dopant is, for example, added in a concentration of 1-20%, preferably 1-10%.

The dopant is either dissolved in the polymer or blended into the polymer. As the polymer layer may be a mixture of polymers, oligomers, monomers and additives, (as outlined above) and can also contain solvent, the dopant can be either dissolved or in any kind of a heterogeneous blend. For example the dopant and the polymer can form a dispersion, an emulsion, a suspension and the like.

Functionalized Polymers

Polymers functionalized with acidic groups are, for example, polymers having at least one —$SO_3H$, —$PO_3H_2$, COOH, substituent.

For example.

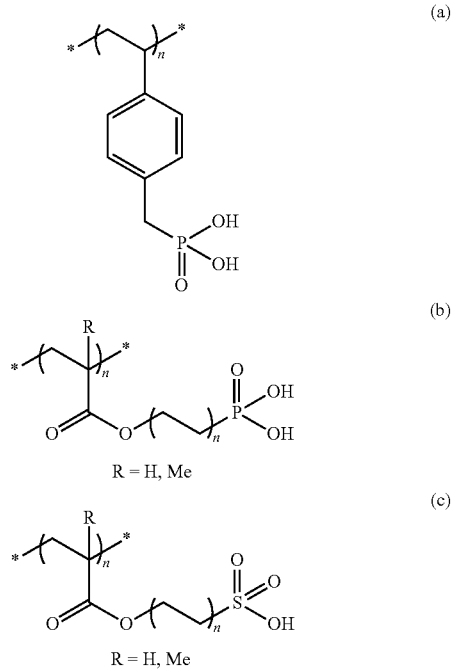

Polymers functionalized with basic groups, are, for example, polymers having a basic nitrogen atom such as an amine group, a basic oxygen atom such as a hydroxyl group or an alkoxy group such as methoxy or ethoxy.

A polymer layer functionalized with a latent acidic or a latent basic group is a polymer generating a free acid or an acidic group or a free base or a basic group upon irradiation with light.

Preferably the dopant is an acid or the polymer is functionalized with an acidic group.

It is also possible to use more than one doped polymer layer, (e.g. a plurality of pressure sensitive adhesive polymers (PSA's) having different concentrations of the dopant and/or different viscosities). The different layers may be side by side and/or on above the other so that the reaction is not smooth but has accelerating or relenting effects.

The Metal Layer/Metal Containing Layer

The time temperature indicator according to the invention comprises a metal layer or a metal containing layer, optionally incorporated into, or onto a substrate material such as, for example, polyolefin or polyester films or paper.

Suitable metals for forming the metal layer are selected from aluminium, copper, silver, iron magnesium, titanium, tin, chromium, zinc, nickel, and alloys of these metals.

Preferred is aluminium.

The thickness of the metal layer is from 1 nm to 1 mm, and preferably from 5 nm to 500 µm.

In one embodiment, the metal layer is a metal containing layer consisting of inks containing metal pigment dispersions.

The wet film weight of the ink layer is from 1 to 50 g/m$^2$, preferably from 2 to 30 g/m$^2$.

Suitable inks belong, for example, to the METASHEEN brand (Ciba specialty chemicals) and METALSTAR, TOPSTAR, ULTRASTAR, ROTOSTAR, PRISMASTAR, PEARLSTAR and MFX brands (Eckart).

In one embodiment the metal layer are metal particles in a polymer matrix.

In one preferred embodiment the doped polymer is polyethylene imine doped with a water soluble salt selected from sodium chloride, potassium iodide, lithium fluoride, potassium chloride, sodium iodide, lithium fluoride, sodium carbonate.

In one preferred embodiment the time temperature indicator has an aluminium metal (and/or metal containing) layer and a polyethylene imine layer doped with potassium iodide.

In one preferred embodiment the doped polymer layer contains polyacrylate or a polymethacrylate and it is doped with an acid.

In another preferred embodiment the doped polymer layer contains polyacrylate or a polymethacrylate and it is doped with a base, with a photolatent acid or with a photolatent base.

In another preferred embodiment, the doped polymer layer is an adhesive which is doped with an acid.

In another preferred embodiment the doped polymer layer is an adhesive doped with a base, with a photolatent acid and with a photolatent base.

Some of the suitable adhesives are commercially available and are selected from, but not limited to, the group consisting of the following manufacturers BASF (ACRONAL A 240, ACRONAL V115, ACRONAL V215, ACRONAL V220, ACRONAL V210, ACRONAL 80D, BUTOFAN LS103), TESA ( . . . ), VEROLIT (1740, 1763, 1764, 1860), DOW chemicals (UCAR, POLYOX), Celanese (Sensitac), POLYMER LATEX (Plextol) etc.

The lab-scale preparation of ACRONAL V115 doped with 5% H$_3$PO$_4$ (85% W/W in water) is given as a non limiting representative example for the preparation of active glue layers. ACRONAL V115 (95 g) is stirred with a propeller-type stirrer (500-600 rpm) which creates a large vortex with a moderate shear. The acid (5 g) is added dropwise. The resulting mixture is stirred for an additional 1-4 hours. The adhesive is applied on the carrier as 40 microns thickness wet film and dried under an air flush at 20° C.-70° C.

The carrier with the dried adhesive is placed on a liner (release ribbon) for storage.

In another non limiting setup, the vinyl monomers corresponding to (a) and (b) and (c) below (typically 1%-20%) are oligomerized and/or polymerized with (meth)acrylates monomers, thus leading to the formation of an inherently reactive acrylic adhesive. Tackifiers, wetting agents, plasticizers, fillers, preservatives and antifoaming agents are also added in some cases.

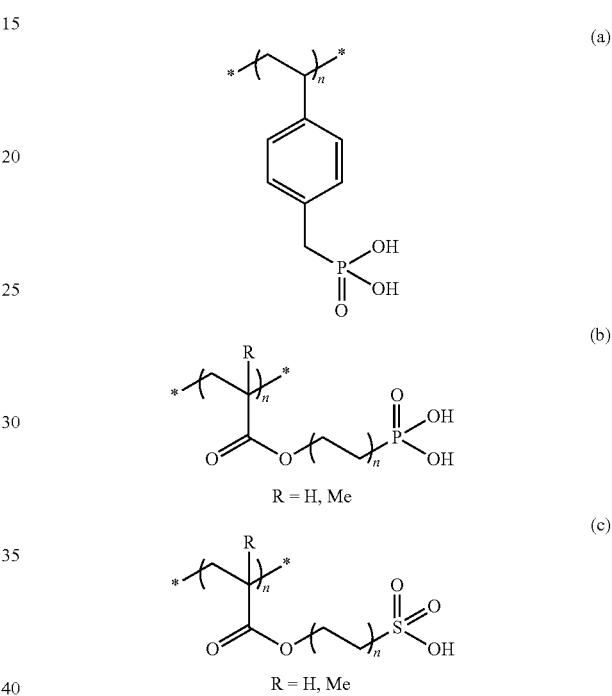

Other dopants are in some cases added as described previously.

(c) for n=1 and R=Me is commercially available.

In another preferred embodiment the viscoelastic liquid (commercial or tailor made adhesive) is doped with a polymeric acid such as poly(vinylbenzyl) phosphonic acid) (a) or poly((meth)acryloyloxyalkyl phosphonic acid) (b)

In one embodiment, the acidic doped adhesive is compounded as a blend of the viscoelastic liquid with the acidic polymers at various ratios (typically 80%-99% and 1%-20%, respectively).

The metal layer or the metal containing layer and the doped polymer layer may be superimposed, or they may lie as parallel stripes, dots or in any other geometry or geometric patterns. The thickness of the doped polymer layer is typically from 0.001 to 1.0 mm, and preferably from 0.001 to 0.1 mm.

The Way to Activate the Time-Temperature Count

Each TTI system needs to be activated at a given time. There are two ways to initiate the activation.

In a one label system the metal layer or the metal containing layer is applied onto a substrate and is in direct contact with the polymer containing the photolatent dopant. Metal layer and polymer layer form one label. The activation is done by irritation with light. For example UV light is used.

A one label system is also a system consisting of one layer composed of metal particles in a polymer matrix, the polymer matrix contains a photolatent dopant that is activated by light.

In a two label system, the metal layer or the metal containing layer is applied onto a substrate and forms one label. The polymer layer containing the dopant is applied onto a substrate and forms a separate label. The activation is made by contacting the labels.

In a one or two layer system where the activity is reduced considerably (practically to zero) by low temperatures, the activation starts by taking the TTI for example out of a freezer.

Preparation

Two Label System

In a further embodiment, the present invention also relates to a method for producing the time temperature indicator as described hereinbefore comprising the steps of a) doping a polymer by adding a salt, an acid or a base to the polymer or preparing a functionalized polymer thus obtaining a reactive polymer, b) applying the polymer of step a) on a substrate thus obtaining one label;

c) applying a metal layer or a metal containing layer on a substrate thus obtaining a second label.

d) activating by applying the reactive polymer label of step b) onto the metal layer of step c)

Step c may be performed by vapour deposition or electrochemical deposition or in any other way. In case the metal containing layer is an ink, the ink is printed onto the substrate.

One Label System

A method for producing the time temperature indicator as described hereinbefore comprising the steps of a) doping a polymer by adding a latent acid or a latent base to the polymer or preparing a functionalized polymer having latent acidic or basic groups thus obtaining a latent reactive polymer, b) activating the latent reactive polymer of step a by irradiation with light thus obtaining a reactive polymer;

c) applying the polymer of step a) on a metal layer or a metal containing layer on a substrate thus obtaining a label whereby placing one layer atop the other may be done either before activation or after or at the same time; or d) adding a metal particles to the polymer layer that contains the latent acid or base or to the functionalized polymer having latent acidic or basic groups and activating by irradiation with 30 light.

The substrate is preferably selected from the group consisting of paper, cardboard, paperboard, a plastic material (polypropylene, polyethylene, polyester) or metal.

The manufacturing process can be carried out using processing technologies suitable for packaging machines, preferably using gravure printing, spray coating, inkjet, blade coating, offset, flexo, spincoating, silk screen printing, curtain coating, metering rod (Meyer rod) coating, slot die (extrusion) coating and/or lamination processes. The entire surface of the packaging material may also be coated by said electrical and/or optical temperature detector/indicator, and if necessary, self-adhesive labels may be manufactured therefrom for attaching on the package. Each layer may also be printed on its respective substrate followed by adhesion thereof with each other e. g. for producing self-adhesive labels. An adhesive layer may optionally be placed between the layers.

The activation of the system (adhesion of two layers for the two labels system and light irradiation for the latent system) may be induced prior to the delivery onto the packaging. The activation may take place after one or more layers are attached to the packaging.

The adhesion of the reactive layer to the metal layer may be carried out by using a device for dispensing labels. One dispenser attaches the label bearing the doped polymer layer to the surface of the metal layer while the second dispenser deposits the combined labels (doped polymer layer+metal layer) atop the surface of the good to which the TTI indicator is to be attached.

A further embodiment is a method of activating and dispensing the claimed TTI label comprising two label dispensers where one dispenser attaches the metal containing label atop the surface of the good to which the TTI indicator is to be attached while the second dispenser deposits the layer bearing the doped polymer layer to the surface of the said metal containing label.

A method of activating and dispensing a TTI label comprising a latent reactive layer by using a label dispenser that is equipped with a light source for activating the photolatent reactive layer.

The time temperature indicator may optionally be coated with a protective layer.

Monitoring the Time Temperature History

The time temperature indication may be achieved electrically or electronically by detecting a time temperature dependent change in the electrical property or properties of the device and/or said metal layer. In the simplest case the electrical property is the resistance.

The time temperature indication may be achieved optically by detecting a change in an optical property (such as for example absorption, transmission, reflectivity) of the device and/or said metal layer itself or optically measuring a prefabricated background of said metal layer which becomes accessible due to the time temperature dependent dissolution, disintegration, reaction, oxidation or any other process inflicted by the reaction of the metal containing layer and polymer layer of said metal layer. For instance, a color change of the metal layer, which is preferably a colored electro-oxidized aluminum layer, is determined either visually by comparing to a reference sample, or using an optical color reader, for example, by detecting a change of light power passing through the TTI. This change can also be observed in a reflective mode.

A. change in electrical conductivity may be measured electrically using a contact device by bringing two electrodes in contact to the time temperature indicator, or by using RF techniques. Here the time temperature indicator is incorporated as a part into a RF tag or RFID. The RFID containing an above described metal/polymer element will change its characteristics upon time and temperature in a well defined fashion.

In one embodiment the metal layer is part of a capacitive device which is characterized by at least two conductive layers i.e. at least two capacitor plates with a viscoelastic polymer containing the dopant top layer acting as the affecting layer and a second thin dielectric/insulating layer between the conductive layers providing high capacitance values.

Here the capacitance of the system changes as a function of the time and temperature by either etching and/or dissolving Instead of a capacitive geometry the metal layer may also be patterned to form the features of a RF tag (antenna, resistor or capacitor). (RF=radio frequency). which change properties (for instance Q factor) upon the time and temperature dependent etching of a metal layer,

FIGURES

The invention is further described by the figures which represent non limiting examples.

FIG. 1 is a resistor

It is a schematic illustration of a resistive TTI comprising one metal layer in contact with a doped polymer layer. The resistance is measured with two electrodes.

The following Table 1a shows the electrical conductivity/resistance recorded in arbitrary units (a.u.) as a function of time at different temperatures. The doped polymer is ACRONAL 10 V115 doped with 7% $H_3PO_4$ (85% in water). The metal is aluminium.

TABLE 1a

| Time (min) | Resistance (a.u.) at 23° C. | Resistance (a.u.) at 14° C. | Resistance (a.u.) at 4° C. |
| --- | --- | --- | --- |
| 0 | 5 | 5 | 5 |
| 200 | 0 | 4.9 | 5 |
| 600 | 0 | 0 | 5 |
| 1000 | 0 | 0 | 5 |
| 1750 | 0 | 0 | 4.8 |
| 2000 | 0 | 0 | 0 |

This example points out the drastic drop in electric potential (conductivity/resistance) of the TTI upon dissolution of the conductive aluminium layer.

The following Table 1b shows also the temperature influence on the reaction rate. The metal layer is PVD aluminium Kurz skt20. (OD=0.67). The doped polymer is ACRONAL V115 doped with 5% $H_3PO_4$ TABLE 1b

| Time (h) | Resistance (a.u.) at 23° C. | Resistance (a.u.) at 15° C. | Resistance (a.u.) at 4° C. | Resistance (a.u.) at 2° C. |
| --- | --- | --- | --- | --- |
| 0 | 4.1 | 4.1 | 4.1 | 4.1 |
| 50 | 0 | 2 | 4.0 | 4.1 |
| 100 | 0 | 0 | 3.8 | 3.9 |
| 150 | 0 | 0 | 3.2 | 3.2 |
| 200 | 0 | 0 | 2.8 | 3.0 |
| 250 | 0 | 0 | 1.8 | 2.0 |
| 300 | 0 | 0 | 0.5 | 0.6 |
| 350 | 0 | 0 | 0.1 | 0.2 |
| 400 | 0 | 0 | 0 | 0 |

The following Table 1c shows a direct correlation of the lifetime of the TTI to the thickness of the aluminium layer. The doped polymer is ACRONAL V115 doped with 4.25% $H_3PO_4$. Different PVD aluminium layers are used.

TABLE 1c

| Time (h) | Resistance (a.u.) Kurz skt 20 OD = 0.7 | Resistance (a.u.) Kurz skt57 OD = 1.7 | Resistance (a.u.) Dor film OD = 2.2 |
| --- | --- | --- | --- |
| 0 | 4.0 | 4.2 | 4.5 |
| 48 | 0 | 4.0 | 4.5 |
| 96 | 0 | 3.6 | 4.4 |
| 144 | 0 | 2.9 | 4.3 |
| 192 | 0 | 2.5 | 4.2 |
| 240 | 0 | 1.7 | 4.1 |
| 288 | 0 | 1.0 | 4.0 |
| 336 | 0 | 0.8 | 3.7 |
| 384 | 0 | 0.3 | 3.5 |

Figure 2:
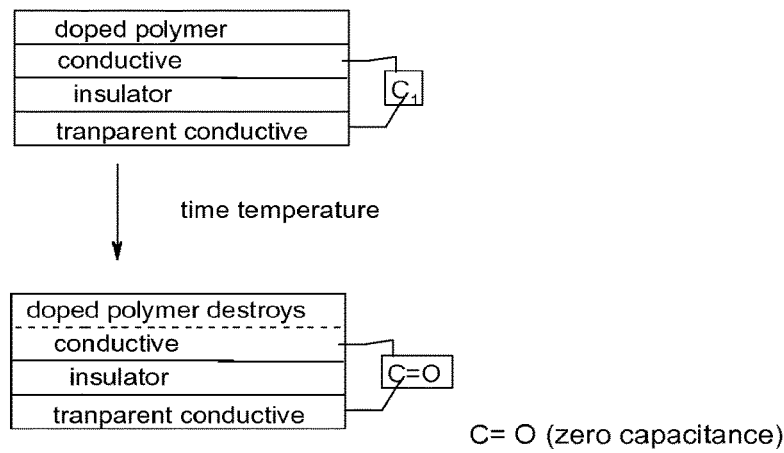
Figure 3:
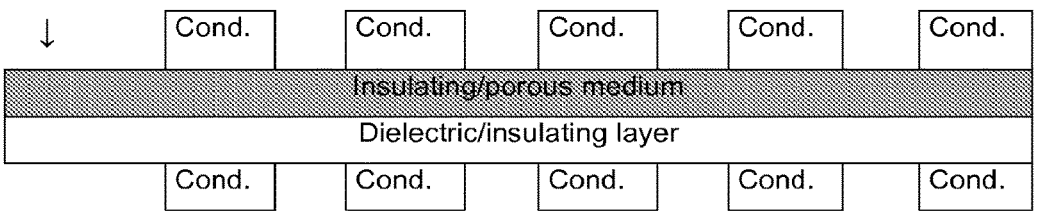
FIG. 3 is a schematic illustration of a TTI structure according to another embodiment of the invention based on changing the dielectric/insulating layer between the capacitor plates.
Figure 3:
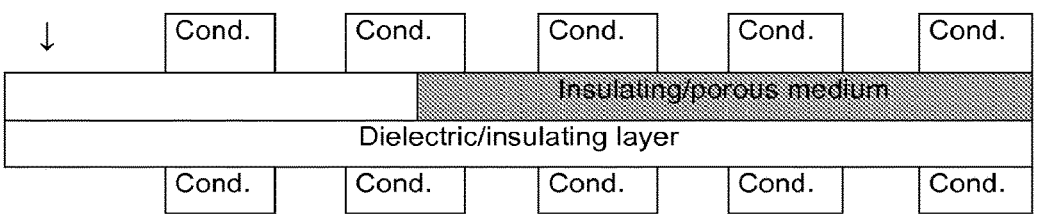

FIGS. 2 and 3 are capacitive devices.

FIG. 2 is a schematic illustration of a TTI structure according to one embodiment of the invention, utilizing a capacitive device which is characterized by two conductive layers with a dielectric/insulating layer in between.

Layer 1 is a transparent conducting layer allowing the visual/optical observation of the etching process of the conducting layer 3, for example an aluminum layer.

The doped polymer is the top layer of FIG. 2 (layer 4). The doped polymer layer is for example polyethylene imine (Mn=60,000 D, 50% in water) doped with 10% KI For creating high values of the capacitance (C) the dielectric/insulating layer 2 (Insulator) is in our example a thin polymer layer (typically polyimide) with a layer thickness of typically 10 to several 100 nanometers (layer two from the bottom). The aluminium layer is destroyed by etching. The system is both eye and machine readable.

The following Table 2a shows the capacitance change of a TTI system as shown in FIG. 2. Due to the etching effect the capacitance decreases. This example demonstrates the effect of a sudden change in temperature (sample moved from 4° C. to 25° C.) on the electrical properties. The doped polymer layer is polyethylene imine (Mn=60,000 D, 50% in water) doped with 10% KI.

TABLE 2a

| Time (h) | Capacity (pF) | remark |
| --- | --- | --- |
| 0 | 3300 | |
| 100 | 3500 | |
| 200 | 3300 | |
| 300 | 3300 | |
| 400 | 3250 | |
| 450 | 0 | Sample moved from 4° C. to 25° |

The following Table 2b demonstrates the effect of the concentration of the inorganic salt on the rate of dissolution of the aluminium and subsequent changes in the electric properties of the TTI. An increase in the concentration of the electrolyte causes an enhancement of the reaction rate.

TABLE 2b

| Time (h) | Capacity (pF) KJ 10% | Capacity (pF) KJ 1% |
| --- | --- | --- |
| 0 | 2250 | 2750 |
| 10 | 250 | 2500 |
| 20 | 0 | 750 |
| 40 | 0 | 100 |
| 60 | 0 | 0 |

FIG. 3 is a schematic illustration of a TTI structure according to another embodiment of the invention based on changing the dielectric/insulating layer between the capacitor plates. The second layer from the bottom is a dielectric/insulating layer, for example a thin polymer layer (typically polyimide) as described at FIG. 2

This dielectric/insulating layer is very important to guarantee high insulating values for the dielectric layer. Dielectric liquids rarely have very high insulation properties as needed for the device. There is an insulating/porous medium capable of letting a dielectric fluid diffuse into the capacitor spacing. If one assumes that the liquid has a high dielectric constant (typically above 1.5 up to high values of 10 and higher) the permeation of the liquid into the capacitor spacing increases the capacitance of the device.

The insulating porous media is, for example, Whatman Nr 5 filter paper or a layer composed of granular insulator such as silica, alumina and alike. The viscoelastic liquid (the doped polymer layer) (PEI–Mn=60000 D+KI) absorbs onto the porous media and diffuses through it, thus causing changes in the capacitance of the system.

Table 3a shows the capacitance change of a TTI system as shown in FIG. 3

The viscoelastic liquid diffuses according to a time-temperature correlation in the direction of the first capacitor (conducting section). The capacity varies sharply when the viscoelastic liquid reaches the first conducting section. This example describes a setup with one conducting section and subsequent single change in capacity. A similar experiment with multiple capacitor sections will bring about multiple increasing steps in the capacity of the system.

TABLE 3a

PEI on paper, room temperature

| Time (hr) | Capacity (pF) |
|---|---|
| 0 | 107 |
| 50 | 112 |
| 100 | 115 |
| 120 | 127 |
| 130 | 135 |
| 140 | 145 |

Yet another example is the usage of the dielectric increase of the capacitance C with time and temperature and combine this with the first described decrease of C with the etching of one (or both) of the conductive layers. Here one would create more complex time/temperature profiles. In this case the capacitance would first increase due to dielectric effects and then decrease due to etching effects.

FIG. 4A-4D show optical systems.

Figure 4A:
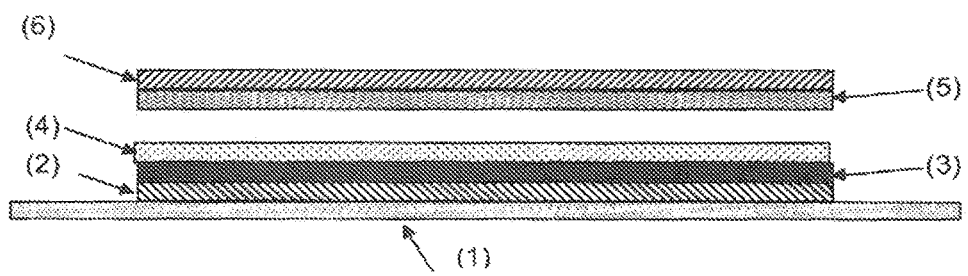
FIG. 4A is a schematic illustration of a TTI structure according to the invention that focuses on the optical properties of the device, looking at the TTI through the doped polymer layer/metal (preferably Al) interface (doped polymer layer on top).

FIG. 4A is a schematic illustration of a TTI structure according to the invention that focuses on the optical properties of the device, looking at the TTI through the doped polymer layer/metal (preferably Al) interface (doped polymer layer on top).

The metal containing layer of the device is placed atop the substrate such as e.g. the package of a perishable good (1). The metal containing layer is composed of a metal layer, preferably an aluminium layer (4), a metal carrier layer such as e.g. a PP film, PE film or paper (3) that is equipped with an adhesive on one side (2).

The reactive label is placed over the metal containing layer and is composed of a doped polymer layer (5) and a carrier layer (6). FIG. 4A shows the device shortly before the reactive label is laminated to the metal containing part.

During storage the doped polymer layer (5) has to be protected to maintain the polymer properties such as e.g. viscosity, humidity, reactivity and the like. An easily removable cover strip is applied to the doped polymer layer. The cover strip may be a silicone film, PET and the like. The carrier layer 6 can also act as protective layer.

The aluminum layer may be produced by one of any known techniques, including vapour deposition, electrode-position, chemical deposition, electroless deposition and even deposited as printed ink (not necessarily conductive). Alternatively, the aluminum layer may be part of the packaging material itself. This aluminum layer, as it is described, is practically time-temperature stable.

The time temperature count of the TTI starts upon contacting the aluminium layer with the reactive label. The doped polymer reacts with the aluminum layer (either chemically or physically) at a rate which is temperature dependent. Different signs may be placed behind the aluminum layer in a way that it is exposed once the aluminum layer is consumed.

Figure 4B:
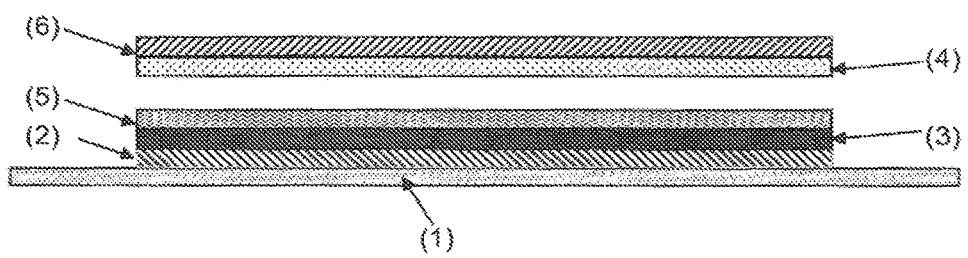

FIG. 4B is also a schematic illustration of a TTI structure according to the invention that focuses on the optical properties of the device, in this embodiment however looking at the TTI through the metal (preferably Al) layer (metal top).

The upper label is the aluminum layer (4) and its carrier such as PP or PE (6). The time temperature count of the TTI starts upon contacting the aluminium layer with a reactive label consisting of a carrier layer such as PP film, PE film or paper (3) that is equipped with an adhesive on one side (2) and a doped polymer (5) that reacts with the aluminum layer. The carrier is placed atop a substrate, such as the package of a perishable good (1).

FIG. 4B shows the device shortly before the reactive label is laminated to the metal containing part.

During storage the doped polymer layer (5) has to be protected as described above under FIG. 4A The major advantage here is that since aluminum is a highly reflective layer and the light does not penetrate it, it looks intact as long as the reaction does not approach its surface that is exposed to the viewer. This offers a nice, close to step function response of the TTI.

Figure 4C:
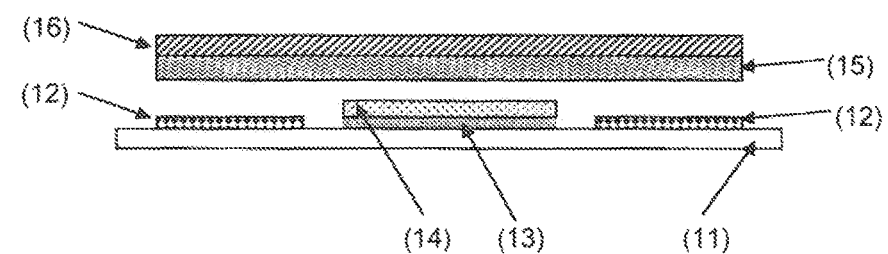
FIG. 4C is a side view of an embodiment for the TTI based on a printable aluminium ink.

FIG. 4C describes a side view of an embodiment for the TTI based on a printable aluminium ink. An informative logo (12) and the background of the TTI (13) are printed on a substrate (11) such as PP, PET, PE, paper, cardboard etc. The printing process can be performed with all known printing and coating techniques such as rotogravure, flexography, inkjet, screen printing, reverse roll, Meyer rod, curtain coating, etc. The aluminium ink (14) is printed on top of the background. The activation begins upon contact with the doped polymer (15) and its carrier (16) such as PP, PE or PET.

Figure 4D:
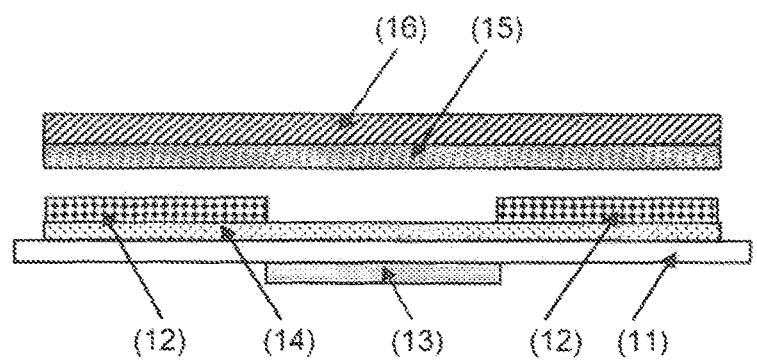
FIG. 4D is a side view of another embodiment where the TTI is based on a physically vapor deposited aluminium (PVD) layer.

FIG. 4D describes a side view of another embodiment where the TTI is based on a physically vapour deposited aluminium (PVD) layer. In this embodiment, a substrate (11) such as PP, PE, PET, or paper etc. is PVD metallized on one side, resulting in a thin metal layer (14), preferably aluminium. The background of TTI (13) is printed on the other side of the substrate. The informative logo (12) is printed directly on top of the metal layer. The ink and printing techniques for the impression of the logo are selected so that the printed layer is non-reactive and non-permeable towards the doped polymer (15), acting as a protective layer for the PVD aluminium, thus preserving a homogeneous background for the logo. Flexographic printing with UV-curable inks is such a suitable printing process.

Figure 4E:
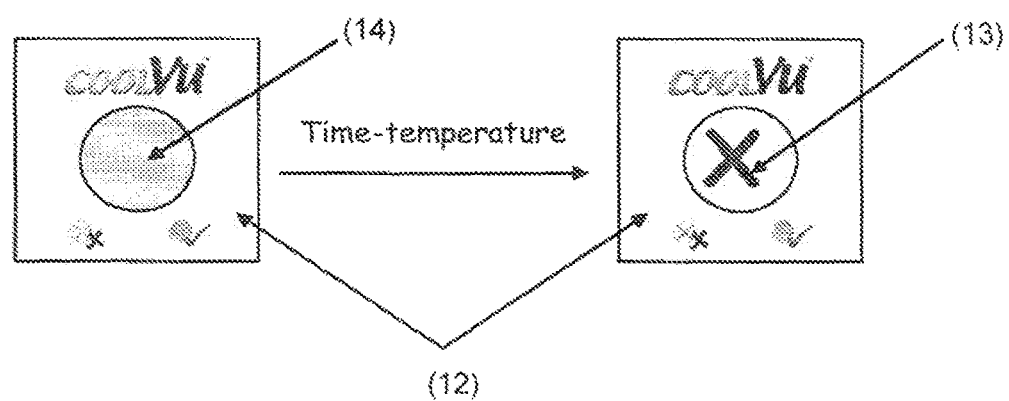
FIG. 4E shows a top view of the optical system TTI before and after application of time-temperature.

FIG. 4E shows a top view of the optical system. A label consisting of an informative logo (12) in the centre of which a metal layer (preferably aluminium) is applied (14). The aluminium layer is etched upon activation (contact with doped polymer) according to a time-temperature correlation, eventually revealing the background (13).

Figure 4F:
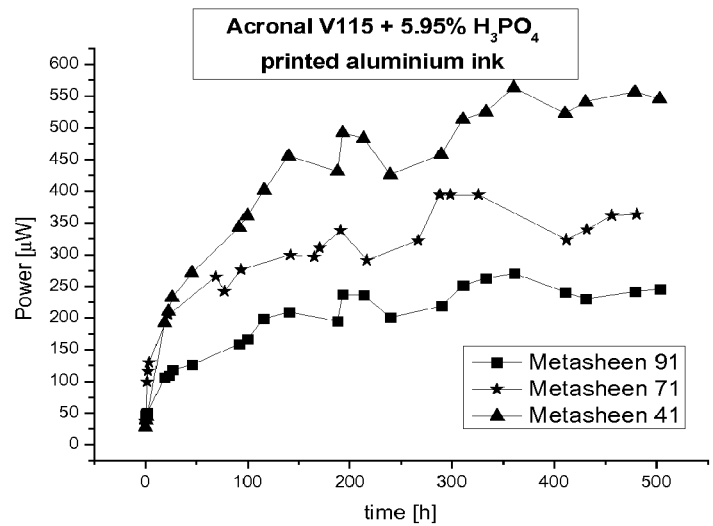
FIG. 4F is a graph showing light transmission as a function of time and at a temperature of 40° C., measured using a TTI setup where the metal layer consists of aluminium inks, based on aluminium pigments.

FIG. 4F refers to a TTI setup where the metal layer consists of aluminium inks, based on METASHEEN® aluminium pigments from Ciba, which were etched with an ACRONAL V115-H$_3$PO$_4$ (5.95%) system. The different pigments are differentiated by their particle size and particle size distribution (particle size of the METASHEEN inks: 91>71>41). The light transmission was recorded in arbitrary units (μWatt) as a function of time and at a temperature of 40° C. The sample reached transparency at about 500 μW. This example shows that the particle size of the metal pigments plays a central role in the rate of dissolution of the metal layer.

Figure 4G:
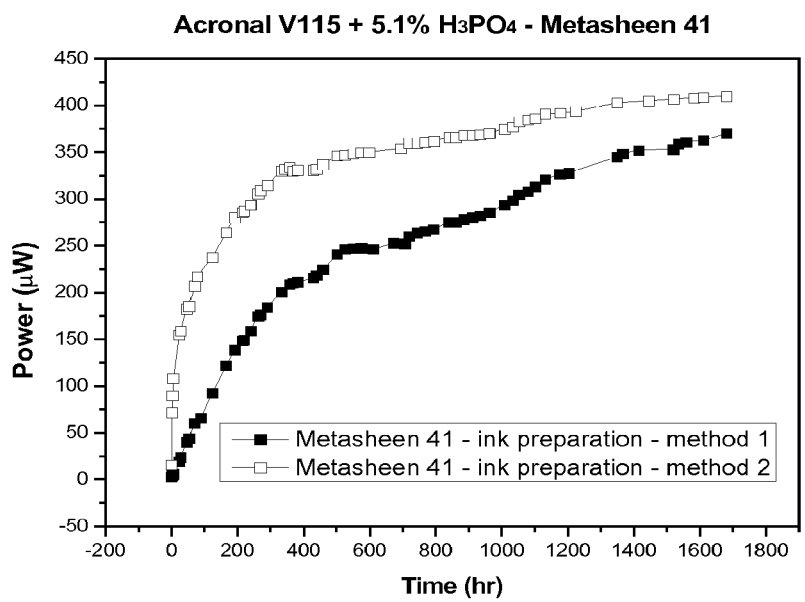
FIG. 4G is a graph showing light transmission as a function of time at 40° C., measured using a TTI setup where the metal layer consists of aluminium inks that were processed into inks by two different methods (varying essentially in the temperature of processing).

FIG. 4G relates to a TTI setup wherein the metal layer consists of two inks based on the METASHEEN®-41 aluminium pigments from Ciba, which were processed into inks by two different methods (varying essentially in the temperature of processing). The aluminium inks were etched with an ACRONAL V115-H$_3$PO$_4$ (5.1%) system at 40° C. The light power was recorded as described above under FIG. 4F. This example illustrates the influence of the ink processing technology on the time-temperature dependence of the metal etching process.

Figure 4H:
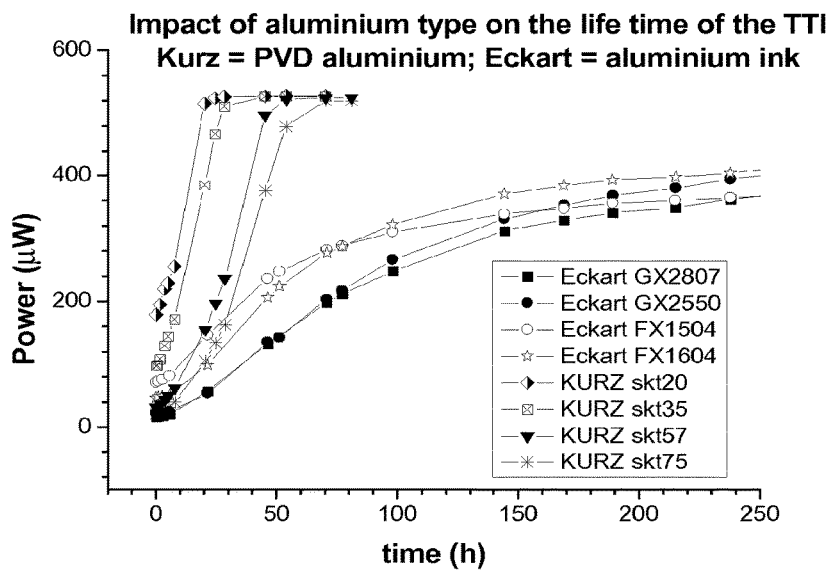
FIG. 4H is a graph showing light transmission as a function of time at 40° C. and of the ink used.

FIG. 4H shows further results obtained with 4.25% H$_3$PO$_4$ in ACRONAL V115 at 40° C. The transparency is recorded as a function of the time and of the ink used.

Figure 4I:
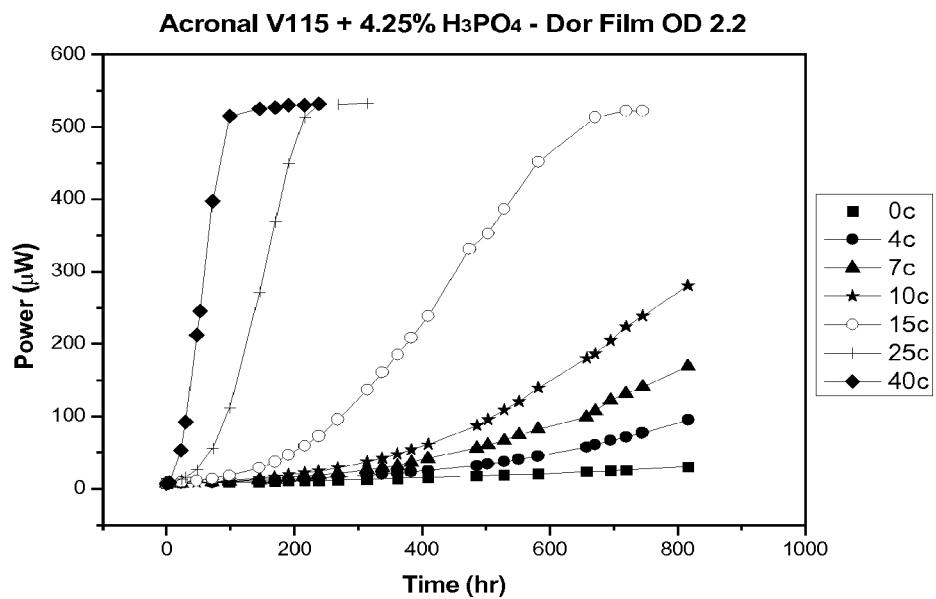
FIG. 4I is a graph showing light transmission as a function of time at various temperatures, measured using a TTI setup where the metal layer consists of a PVO (physical vapor deposition) aluminum layer.

FIG. 4I relates to a TTI setup where the metal layer consists of a PVD (physical vapor deposition) aluminium layer (OD=2.2). The etching process was recorded at 0, 4, 7, 10, 15, 25, and 40° C. The doped polymer is an ACRONAL V115+4.25% H$_3$PO$_4$ etching system. A clear time-temperature relationship is observed.

Figure 4J:
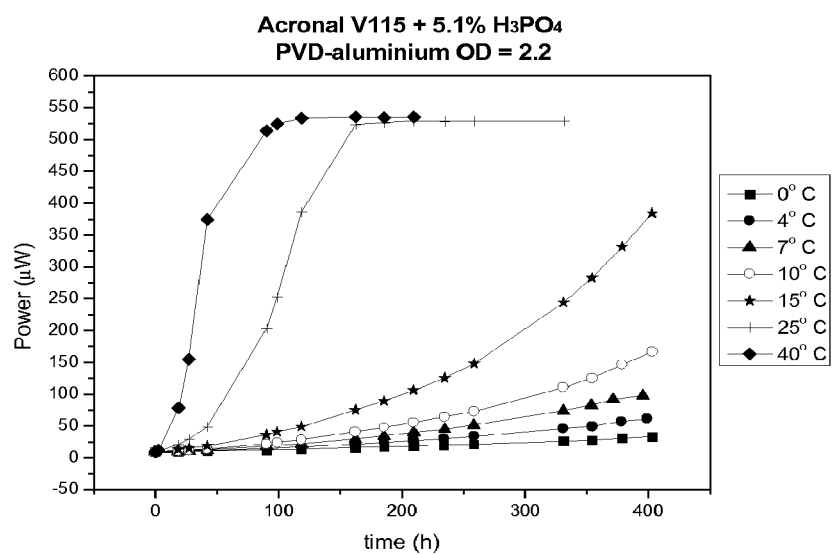
FIG. 4J is a graph showing light transmission as a function of time at various temperatures, measured using another TTI setup where the metal layer consists of a PVO (physical vapor deposition) aluminium layer.

FIG. 4J relates to a TTI setup where the metal layer consists of a PVD (physical vapor deposition) aluminium layer (OD=2.2). The etching process was recorded at 0, 4, 7, 10, 15, 25, and 40° C. The doped polymer is an ACRONAL V115++5.1% H$_3$PO$_4$ etching system.

A clear time-temperature relationship is observed.

The invention claimed is:

1. Components for making a time temperature indicator (TTI), comprising:
    a first label comprising:
        a first carrier layer,
        a metal layer or a metal-containing layer disposed on one side of said first carrier layer, and
        an adhesive layer, said adhesive layer being disposed on the opposite side of said first carrier layer as said metal layer or said metal-containing layer; and
    a second label comprising a second carrier layer and, disposed thereon, a photolatent polymeric layer comprising a photolatent polymeric matrix, wherein (a) the polymer of the polymeric matrix is functionalized with photolatent acidic or photolatent basic groups, or (b) the polymeric matrix contains a dopant that is a photolatent acid or a photolatent base, whereby, upon irradiation with light, an acid or a base is formed from the photolatent acidic or basic groups or from the photolatent acid or photolatent base, which acid or base reacts with said metal layer or metal containing layer when brought into contact therewith.

2. Components according to claim 1, wherein said photolatent polymeric layer comprises a photolatent polymeric matrix of (b), wherein said dopant is a photolatent acid.

3. Components according to claim 1, wherein said photolatent polymeric layer comprises a photolatent polymeric matrix of (b), wherein said dopant is a photolatent base.

4. Components according to claim 1, wherein said photolatent polymeric layer comprises a photolatent polymeric matrix of (b), wherein said dopant is present in said polymeric matrix in a concentration of 1-20%.

5. Components according to claim 4, wherein the dopant is present in a concentration of 1-10%.

6. Components according to claim 1, wherein the metal of said metal layer or metal-containing layer is selected from the group consisting of aluminum, copper, silver, iron, magnesium, tin, chromium, zinc, nickel, titanium and alloys of these metals.

7. Components according to claim 6, wherein said metal layer or metal-containing layer is an aluminum layer.

8. Components according to claim 1, wherein said metal layer or metal-containing layer is a metal-containing layer comprising an ink based on metal pigment dispersions.

9. Components according to claim 1, wherein said metal layer or metal-containing layer is a polymer matrix containing metal particles.

10. Components according to claim 1, wherein said metal layer or metal-containing layer is part of a resistor device.

11. Components according to claim 1, wherein said metal layer or metal-containing layer is part of a capacitive TTI device which is characterized by at least two conductive layers with a dielectric/insulating layer in between.

12. A method of using the TTI components of claim 1, comprising
    attaching said first label atop a surface of a good whose time-temperature is to be monitored, or atop the packaging of such good, such that said adhesive layer is in contact with said good or packaging; and
    either before, after or at the same time as the attaching step, disposing said second label on the surface of the said first label.

13. Components according to claim 1, wherein said metal layer or said metal-containing layer of said first label comprises a metal containing layer and said metal containing layer comprises a metal layer and a protective layer overlying a portion of said metal layer, said protective layer being non-reactive and non-permeable towards the acid or base formed, upon irridation with light, from the photolatent polymeric layer used in said second label.

14. Components according to claim 1, wherein the polymeric matrix of said photolatent polymeric layer is an adhesive.

15. A method of producing a time-temperature indicator according to claim 1, comprising:
    forming a first label comprising said metal layer or metal-containing layer on said first carrier layer;
    forming a second label comprising said photolatent polymeric layer on said second carrier layer; and
    affixing the first and second labels to one another such that the first and second carrier layers are on the outside.

16. A method according to claim 15, wherein the polymer of said photolatent polymeric layer is an adhesive.

17. A method for producing a time temperature indicator, comprising the steps of:
    a) applying a metal layer or a metal-containing layer onto a substrate, thus obtaining a first label;
    b) obtaining a photolatent reactive polymer comprising (1) a doped polymer containing a photolatent acid or a photolatent base a dopant, or (2) a functionalized polymer which is functionalized with photolatent acidic groups or photolatent basic groups, whereby, upon irradiation of the photolatent reactive polymer with light, an acid or a base is formed from the photolatent acidic or basic groups or from the photolatent acid or photolatent base, which acid or base reacts with said metal layer or metal-containing layer when brought into contact therewith;

c) applying the polymer of step b) to a substrate, thus obtaining a second label;

d) applying the polymer of said second label onto the metal layer or metal containing layer of said first label; and e) either before, after or at the same time as the applying of step (d), irradiating the photolatent reactive polymer with light.

18. A time temperature indicator comprising a metal layer or a metal containing layer in contact with a doped polymer layer, said doped polymer layer comprising a polymer and a dopant, wherein the dopant is a photolatent acid or a photolatent base, the dopant having properties such that, upon irradiation with light, an acid or a base is formed from the photolatent acidic or basic groups or from the photolatent acid or photolatent base, which acid or base reacts with the metal of said metal layer or said metal containing layer when brought into contact therewith.

19. A time temperature indicator according to claim 18, wherein said dopant is a photolatent acid having properties such that, upon irradiation with light, an acid is formed from the photolatent acid, which acid reacts with said metal layer or said metal containing layer when brought into contact therewith.

20. A time temperature indicator according to claim 18, wherein said dopant is a photolatent base having properties such that, upon irradiation with light, a base is formed from the photolatent base, which base reacts with said metal layer or said metal containing layer when brought into contact therewith.

21. A method for producing the time temperature indicator as described in claim 18, comprising the steps of:

a) obtaining said doped polymer having said dopant incorporated in said polymer;

b) applying a layer of the doped polymer of step a) onto said metal layer or metal-containing layer; and c) either before, after or at the same time as said applying step b), activating said dopant by irradiation with light.

22. A time temperature indicator comprising at least one metal in contact with at least one polymer, said at least one polymer being functionalized with photolatent acidic or photolatent basic groups, the functionalized polymer having properties such that, upon irradiation with light, an acid or a base is formed from the photolatent acidic or basic groups or from the photolatent acid or photolatent base, that which acid or base reacts with said at least one metal when brought into contact therewith.

23. The time temperature indicator according to claim 22, wherein said functionalized polymer comprises monomers corresponding to (a), (b) or (c)

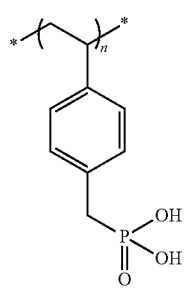

(a)

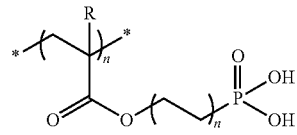

(b)

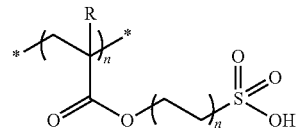

(c)

wherein n is 1 or more, and R is H or Me.

24. Components according to claim 1, wherein said second label further comprises a second carrier layer that carries said photolatent polymeric layer.

25. A method of activating and dispensing a TTI label according to claim 24, comprising:

attaching said second label to said first label such that the surface of the metal layer or the metal-containing layer of said first label is in contact with the photolatent polymeric layer of said second label, to form a combined label;

depositing the combined label atop the surface of a good whose time-temperature is to be monitored; and either before, after or at the same time as the attaching step, irradiating the photolatent polymeric layer with light.

26. A time temperature indicator comprising a photolatent polymeric layer comprising metal particles within a polymeric matrix, wherein (a) the polymer of the polymeric matrix is functionalized with photolatent acidic or photolatent basic groups, or (b) the polymeric matrix further contains a dopant that is a photolatent acid or a photolatent base, whereby, upon irradiation with light, an acid or a base is formed from the photolatent acidic or basic groups or from the photolatent acid or photolatent base, which acid or base reacts with said metal particles when brought into contact therewith.

27. A time-temperature indicator, comprising:

a first label comprising
a first carrier layer,
a metal layer or a metal-containing layer disposed on one side of said first carrier layer, and
an adhesive layer, said adhesive layer being disposed on the opposite side of said first carrier layer as said metal layer or said metal-containing layer; and
a second label comprising a second carrier layer and, disposed thereon, a photolatent doped polymer layer, said photolatent doped polymer comprising a polymer and a dopant, wherein
said dopant is one or more photolatent acid or photolatent base, the dopant having properties such that, upon irradiation with light, an acid or a base is formed from the photolatent acidic or basic groups or from the photolatent acid or photolatent base, which acid or base reacts with the metal of said metal layer or metal-containing layer when brought into contact therewith, wherein said second label is affixed to said first label such that the doped polymer layer of said second label is facing said metal layer or metal-containing layer of said first label.

28. A perishable good that is optionally in a package, onto which, or onto the package of which, is attached a time-temperature indicator in accordance with claim 27.

* * * * *